(12) United States Patent
Okano et al.

(10) Patent No.: US 8,518,880 B2
(45) Date of Patent: Aug. 27, 2013

(54) THERAPEUTIC AGENT FOR SPINAL CORD INJURIES

(75) Inventors: Hideyuki Okano, Tokyo (JP); Yoshiaki Toyama, Tokyo (JP); Masaya Nakamura, Tokyo (JP); Akio Iwanami, Tokyo (JP); Kazuya Kitamura, Tokyo (JP); Toshikazu Nakamura, Kyoto (JP); Hiroshi Funakoshi, Hokkaido (JP); Keigo Hanada, Osaka (JP)

(73) Assignees: Keio University, Tokyo (JP); Osaka University, Osaka (JP); Kringle Pharma Inc., Osaka (JP)

( * ) Notice: Subject to any disclaimer, the term of this patent is extended or adjusted under 35 U.S.C. 154(b) by 9 days.

(21) Appl. No.: 12/548,881

(22) Filed: Aug. 27, 2009

(65) Prior Publication Data

US 2010/0081617 A1   Apr. 1, 2010
US 2012/0021040 A9   Jan. 26, 2012

Related U.S. Application Data

(63) Continuation of application No. PCT/JP2008/053557, filed on Feb. 28, 2008, which is a continuation-in-part of application No. PCT/JP2007/053804, filed on Feb. 28, 2007.

(51) Int. Cl.
*A61K 38/18* (2006.01)

(52) U.S. Cl.
USPC .......................... 514/9.5; 514/17.7; 514/17.9

(58) Field of Classification Search
None
See application file for complete search history.

(56) References Cited

U.S. PATENT DOCUMENTS

| 6,143,714 | A | * | 11/2000 | Wong et al. ............... 514/8.3 |
| 7,033,608 | B1 | * | 4/2006 | Jevanthi et al. ............ 424/490 |
| 2004/0265283 | A1 | | 12/2004 | Morishita |
| 2008/0274960 | A1 | | 11/2008 | Amano et al. |

FOREIGN PATENT DOCUMENTS

| JP | 2007-077125 | | 3/2007 |
| JP | 2007077125 A | * | 3/2007 |
| JP | 2007-238487 | | 9/2007 |
| JP | 2007-238487 A | * | 9/2007 |
| WO | WO 2004/021992 | * | 3/2004 |
| WO | WO2007-032396 | | 3/2007 |
| WO | WO 2007/032396 | * | 3/2007 |
| WO | WO 2007/032396 A1 | | 3/2007 |

OTHER PUBLICATIONS

Thuret et al., Nature Reviews Neuroscience, 7:628-43, Aug. 2006.*
Iwanami, Akio et al., "Effect of Hepatocyte Growth Factor on Spinal Cord Injury" The Journal of the Japanese Orthopaedic Association, 2005, p. S764, vol. 79, No. 8.
Kato, Naoki et al., "Nonviral HVJ (hemagglutinating virus of Japan) liposome-mediated retrograde gene transfer of human hepatocyte growth factor into rat nervous system promotes functional and histological recovery of the crushed nerve" Neuroscience Research, 2005, pp. 299-310, vol. 52.
Kitamura, Kazuya et al., "Effect of Hepatocyte Growth Factor on Spinal Cord Injury" The Journal of the Japanese Orthopaedic Association, 2006, p. S884, vol. 80, No. 8.
Kitamura, Kazuya et al., "Effect of Hepatocyte Growth Factor on Injured Spinal Cord" Journal fo the Japan Spine Research Society, 2006, p. 557, vol. 17, No. 1.
Shi, Enyi et al., "Nonviral gene transfer of hepatocyte growth factor attenuates neurologic injury after spinal cord ischemia in rabbits" Journal of Thoracic and Cardiovascular Surgery, Oct. 2006, pp. 941-947, vol. 132, No. 4.
Kitamura et al., "Human Hepatocyte Growth Factor Promotes Functional Recovery in Primates after Spinal Cord Injury" PLos ONE 6(11): e277706, vol. 6, Issue 11, Nov. 2011.

* cited by examiner

*Primary Examiner* — Marianne P Allen
(74) *Attorney, Agent, or Firm* — Knobbe Martens Olson & Bear LLP

(57) ABSTRACT

Disclosed is a therapeutic agent effective for the fundamental treatment of a spinal cord injury and a demyelinating disease. Specifically disclosed are a therapeutic agent for a spinal cord injury and a therapeutic agent for a demyelinating disease, each of which comprises an HGF protein as an active ingredient.

5 Claims, 5 Drawing Sheets

THERAPEUTIC AGENT FOR SPINAL CORD INJURIES

CROSS REFERENCE TO RELATED APPLICATIONS

This application is a continuation of and claims the benefit of priority to PCT International Application Number PCT/JP2008/053557, filed Feb. 28, 2008, which is a continuation in part of and claims the benefit of priority of PCT international Application number PCT/JP2007/053804, filed Feb. 28, 2007; all of which are hereby expressly incorporated by reference in their entireties.

BACKGROUND OF THE INVENTION

1. Field of the Invention

The present invention relates to a therapeutic agent for spinal cord injuries, and more particularly to a therapeutic agent for spinal cord injuries in which hepatocyte growth factor (abbreviated below as "HGF") protein serves as the active ingredient. The invention also relates to a therapeutic agent for demyelinating diseases in which HGF protein serves as the active ingredient 2. Description of the Related Art The term "spinal cord injury" (SCI) refers to a clinical state that presents peripheral motor, sensory and autonomous nervous system paralysis below the site of injury to the spinal cord parenchyma from trauma such as dislocation-fracture of the spine as a result of, for example, a traffic accident or a fall from a high place.

The number of spinal cord injury patients is currently about 100,000 in Japan, and some 250,000 in the United States. Each year, the number of such patients increases by at least 5,000 in Japan and at least 10,000 in the U.S.

With recent advances in medical care, the survival rate following injury has risen, and remarkable advances have been made also in methods of reconstructive surgery for spinal cord injuries that are intended to check the progression of disability. As a consequence, success is starting to be achieved in checking secondary neurological deterioration as well. In addition, owing to improvements in rehabilitation technology and the development of supportive devices (electric-powered wheelchairs, etc.), the activities of daily living (ADL) of the patient have improved. However, because of the absence of effective methods for fundamentally treating basic spinal cord injuries (i.e., nerve protection from neurological injury and nerve regeneration), there exist today large numbers of such patients who are unable to relieve themselves, do manual labor or walk without the assistance of others.

HGF was initially identified as a powerful mitogen for mature hepatocytes, and in 1989 was genetically cloned (Biochem. Biophys. Res. Commun. 122, 1450-1459 (1984) and Nature 342, 440-443 (1989)). Although discovered as hepatocyte growth factor, from numerous recent studies in expression and functional analysis that include knockout/knockin mouse techniques, HGF has also been found to be a novel neurotrophic factor (Nat. Neurosci. 2, 213-217 (1999) and Clin. Chim Acta., 327, 1-23 (2003)).

In WO 03/045439, working examples are described in which the effects of the HGF gene on Parkinson's disease model rats were behaviorally and histologically investigated. The experimental results presented therein indicate that the prior administration of HGF gene had the effect of protecting dopamine neurons in the mesencephalic substantia nigra from the neurotoxin 6-hydroxydopamine (6-OHDA). WO 03/045439 also states that, based on these experimental results, the HGF gene can be used in the treatment of not only Parkinson's disease, but other neurological disorders as well, including Alzheimer disease, spinocerebellar degeneration, multiple sclerosis, striatonigral degeneration (SND), spinal muscular atrophy (SMA), Huntington chorea, Shy-Drager syndrome, Charcot-Marie-Tooth disease (CMT), Friedreich ataxia, myasthenia gravis, moyamoya disease, amyloidosis, pick disease, subacute myeloopticoneuropathy, dermatomyositis/polymyositis, Creutzfeldt-Jacov disease, Behcet syndrome, systemic lupus erythematosus (SLE), sarcoidosis, periarteritis nodosa (PN), ossification of posterior longitudinal ligament, diffuse spinal canal stenosis, mixed connective tissue disease (MCTD), diabetic peripheral neuritis and ischemic cerebrovascular disorders (e.g., cerebral infarction, cerebral hemorrhaging), and moreover mentions spinal cord injuries as one such type of neurological disorder.

However, 6-OHDA is a special synthetic toxin which has a specific effect on neurons that synthesize catecholamines (specifically, noradrenaline-, adrenaline- and dopamine-producing neurons), and does not exhibit any toxicity against the neurons which are reportedly degenerated or killed in most of the diseases listed above. Therefore, it is impossible to predict the effects on the above disorders, including spinal cord injuries, from the neuronal cell death-suppressing effects by 6-OHDA. In addition, WO 03/045439 makes no mention of the therapeutic effects of administering HGF protein.

The Journal of the Japanese Orthopaedic Association, Vol. 79, No. 8, pS764 (Aug. 25, 2005) mentions that, when a virus vector containing the HGF gene (an HGF-expressing virus vector) was injected into the spinal cord of rats at the tenth thoracic vertebra and a vertebral crushing injury was then created at the same site, the recovery of lower limb motor function was observed in subsequent evaluations of motor function.

Yet, in spite of the fact that spinal cord injuries generally arise from external trauma suffered in accidents and the like, in The Journal of the Japanese Orthopaedic Association, Vol. 79, No. 8, pS764 (Aug. 25, 2005), the HGF-expressing virus vector was injected 3 days prior to the thoracic vertebral crushing injury. Clearly, it is impossible to predict in this way the occurrence of an accident and the site of injury and to locally administer HGF-expressing virus vector beforehand.

Moreover, the condition of a spinal cord injury patient is likely to be unstable for 72 hours following the trauma, which may make it very difficult to insert a catheter for intrathecal administration. Determining the proper period of administration is thus important.

In addition, there are a number of conceivable problems, such as the difficultly of controlling the amount of protein expressed in conventional HGF gene therapy, the danger with some gene expression vectors of triggering an immune response with repeated administration, and the possibility with some gene expression vectors of introducing genes into the genome.

The nerve fibers of myelinated nerves, including the nerves of the spinal cord, are covered with a sheath composed of a layer of lipoprotein called myelin. This myelin sheath functions as an insulator for the nerve fibers, enabling saltatory conduction by the myelinated nerve. The destruction of this myelin sheath is referred to as demyelination. When demyelination occurs, a variety of neurological symptoms arise due to a dramatic slowing of neurotransmission. Diseases accompanied by such demyelination are generally referred to as demyelinating diseases, and typically include, for example, multiple sclerosis. Spinal cord injuries, too, are generally accompanied by demyelination.

Multiple sclerosis is a slowly progressing central nervous system disease characterized by the formation of disseminated demyelinating plaques. The incidence of multiple sclerosis is about 50 to 100 cases per 100,000 people in Europe and the United States, and is about 1 to 5 cases per 100,000 people in Japan. The symptoms vary widely from individual to individual, and may include loss of vision, double vision, nystagmus, articulation disorders, weakness, abnormal sensations, bladder problems and mood swings. The disease progresses with the repeated remission and resumption of such symptoms. The cause, while not yet determined, is suspected to be an immunological abnormality. Hence, as with other demyelinating diseases, no fundamental treatment currently exists.

As indicated above, although methods involving the injection of an HGF gene-containing virus vector (HGF expression virus vector) are known, it is also known that viruses such as a herpes virus (HSV) or an adenovirus produce a concentration-dependent inflammatory reaction in the brain when such viruses are introduced into the brain, inviting demyelination (WO 05/100577).

Therefore, from this perspective as well, treatment methods involving the use of an HGF gene-containing virus vector clearly do not constitute a fundamental approach toward the treatment of demyelinating disease. A desire thus exists for the establishment of a method of treatment that does not invite demyelination.

SUMMARY OF THE INVENTION

Problems to be Solved by the Invention

An object of the invention is to provide an agent which is capable of treating spinal cord injuries and demyelinating diseases by a simple and convenient method that does not involve the use of a gene.

Means for Solving the Problems

The inventors have conducted extensive investigations in order to overcome the above problems. As a result, they have discovered that HGF protein has the most highly sought after functional regenerating effects in spinal cord injury treatment, including a demyelination inhibiting effect and a 5HT nerve regenerating effect, making HGF protein useful as a therapeutic agent for spinal cord injuries. Moreover, the inventors have also found that HGF protein is useful as a therapeutic agent for demyelinating diseases. These discoveries ultimately led to the present invention.

Accordingly the invention relates to:

(1) a therapeutic agent for treating spinal cord injuries, comprising HGF protein as an active ingredient;

(2) the therapeutic agent according to (1) above, wherein the HGF protein is a protein having the amino acid sequence of SEQ ID NO: 1 or 2, a protein having substantially the same amino acid sequence as the amino acid sequence of SEQ ID No: 1 or 2 and having substantially the same activity as HGF, or a peptide which is a partial peptide of one of said proteins and has substantially the same activity as HGF;

(3) the therapeutic agent according to (1) above, wherein the HGF protein is a protein having the amino acid sequence of SEQ ID NO: 2;

(4) the therapeutic agent according to any of (1) to (3) above, wherein the agent is adapted for localized use at a site of spinal cord injury;

(5) the therapeutic agent according to (4) above, wherein the agent is in the form of an injectable preparation for intrathecal administration;

(6) the therapeutic agent according to (4) above, wherein the agent is in the form of an injectable preparation for intrathecal administration by a sustained-release pump;

(7) the therapeutic agent according to any of (1) to (6) above, wherein the agent is for inhibiting spinal cord nerve demyelination;

(8) a therapeutic agent for treating spinal cord injuries, which comprises HGF protein as an active ingredient, and which is administered within 2 weeks following a spinal cord injury;

(9) a therapeutic agent for treating spinal cord injuries, which comprises HGF protein as an active ingredient, and which is administered within 4 days following a spinal cord injury;

(10) a method for treating spinal cord injuries, the method being comprised of administering an effective dose of HGF protein to a spinal cord injury patient;

(11) a use of HGF protein for manufacturing an agent for treating spinal cord injuries;

(12) an HGF protein for treating spinal cord injuries;

(13) a therapeutic agent for treating a demyelinating disease, comprising HGF protein as an active ingredient;

(14) the therapeutic agent according to (13) above, wherein the demyelinating disease is a disease selected from among multiple sclerosis, Devic disease, Balo's concentric sclerosis, acute disseminated encephalomyelitis (ADEM), Schilder disease, subacute sclerosing panencephalitis (SSPE), progressive multifocal leukoencephalopathy (PML), Binswanger disease, hypoxic encephalopathy, central pontine myelinolysis, Guillain-Barre syndrome, Fischer syndrome and chronic inflammatory demyelinating polyradiculoneuropathy (CIDP);

(15) the therapeutic agent according to (13) or (14) above, wherein the HGF protein is a protein having the amino acid sequence of SEQ ID NO: 1 or 2, a protein having substantially the same amino acid sequence as the amino acid sequence of SEQ ID NO: 1 or 2 and having substantially the same activity as HGF, or a peptide which is a partial peptide of one of said proteins and has substantially the same activity as HGF;

(16) the therapeutic agent according to (13) or (14) above, wherein the HGF protein is a protein having the amino acid sequence of SEQ ID NO: 2;

(17) the therapeutic agent according to any of (13) to (16) above, wherein the agent is adapted for localized use at a site of disease;

(18) the therapeutic agent according to (17) above, wherein the agent is in the form of an injectable preparation for intrathecal administration;

(19) the therapeutic agent according to (17) above, wherein the agent is in the form of an injectable preparation for intrathecal administration by a sustained-release pump;

(20) a method for treating a demyelinating disease, the method being comprised of administering an effective dose of HGF protein to a patient with a demyelinating disease;

(21) the use of HGF protein for manufacturing a therapeutic agent for treating a demyelinating disease; and

(22) an HGF protein for treating a demyelinating disease.

Advantageous Effect of the Invention

The therapeutic agent of the invention produces outstanding therapeutic effects against spinal cord injuries and demyelinating diseases. The therapeutic agent of the invention also has the advantage that it is free from the problems associated with gene therapy. In addition, the therapeutic agent of the invention has the advantage that it effectively inhibits and treats the demyelination of myelinated nerves that occurs in spinal cord injuries and demyelinating diseases (e.g., multiple sclerosis). Furthermore, since the therapeutic agent of the invention does not require the use of a virus vector such as HSV or an adenovirus, it does not invite demyelination. A further advantage of the therapeutic agent of the invention is that, unlike gene therapy, the amount supplied or dose of the active ingredient HGF can be easily adjusted, in addition to which the time of administration can be adjusted and administration can be carried out either repeatedly or continuously.

DETAILED DESCRIPTION OF THE PREFERRED EMBODIMENT

Figure 1:
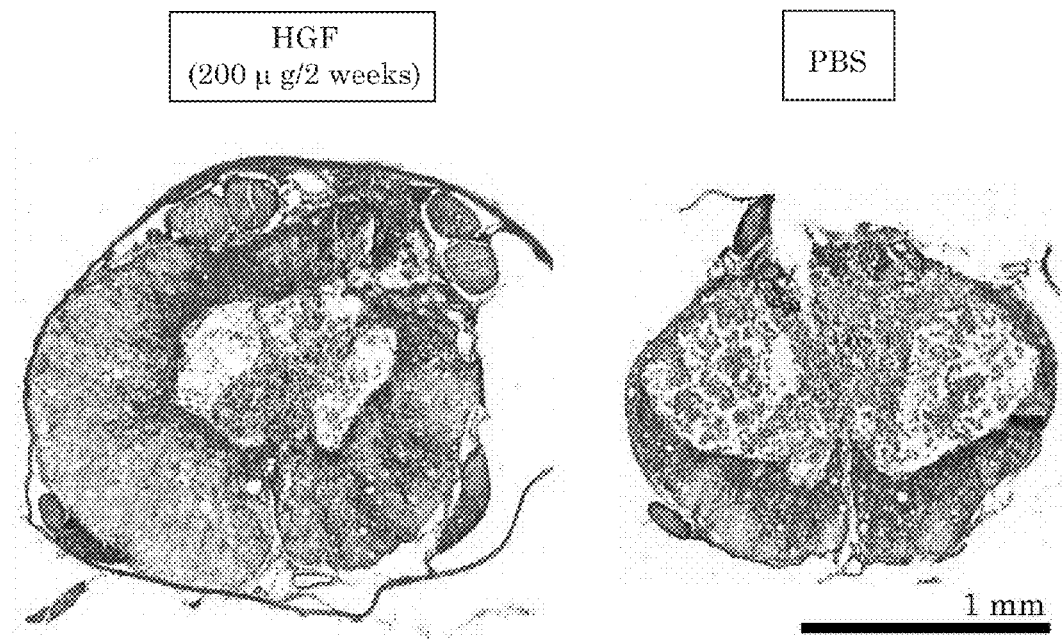
FIG. 1 shows Hematoxylin-Eosin (HE) stained images of spinal cord tissue following a spinal cord injury from an HGF protein group given 200 µg/2 weeks of HGF protein starting immediately after spinal cord injury, and of spinal cord tissue from a control group.

The HGF protein used in the present invention is a known substance. HGF protein prepared by any of various methods may be used, provided it has been purified to a degree that enables its use as a medication. HGF protein can be prepared by, for example, growing primary culture cells or cells from an established cell line that produce HGF protein, followed by separation and purification of the HGF protein from the culture supernatant. Alternatively, use may be made of a genetic engineering technique which entails integrating a gene that encodes the HGF protein into a suitable vector, inserting the vector into a suitable host cell to effect transformation, and obtaining the desired recombinant HGF protein from a culture supernatant of the transformant (e.g., see Japanese Patent Application Laid-open No. H5-111382; and Biochem. Biophys. Res. Commun. Vol. 163, p. 967 (1989)). The host cell is not subject to any particular limitation. For example, suitable use may be made of any of various types of host cells hitherto employed in genetic engineering techniques, such as *Escherichia coli*, yeasts or animal cells. The HGF protein thus obtained, so long as it has substantially the same activity as HGF protein of natural origin, may have on the amino acid sequence thereof one or more (e.g., from 1 to 8; the same applies below) substituted, deleted or added amino acids, or may similarly have substituted, deleted or added sugar chains. Examples of such HGF proteins include the five-amino-acid-deleted-type HGF protein described below. Here, with regard to the amino acid sequence, the phrase "one or more substituted, deleted or added amino acid" means that a number (from one to a plurality) of amino acids have been substituted, deleted, or added by a known technical method such as a genetic engineering technique or site-specific mutagenesis, or naturally. The HGF protein having substituted, deleted or added sugar chains may be, for example, an HGF protein obtained by treating with enzyme or the like a sugar chain added to a natural HGF protein, an HGF protein in which the amino acid sequence at the sugar chain addition site has been altered so that sugar chain addition does not occur, or an HGF protein in which the amino acid sequence has been altered so that a sugar chain is added at a different site than the natural sugar chain addition site.

In addition, proteins having at least about 80% homology, preferably at least about 90%, more preferably at least about 95% homology with the amino acid sequence of the HGF protein, and substantially acting as HGF may be included. In connection with the above-mentioned amino acid sequences, "homology" refers to the degree of agreement in the amino acid residues making up the respective amino acid sequences in comparison of the primary structures of proteins.

Examples of the above HGF proteins include the amino acid sequences of SEQ ID NO: 1 and 2. The HGF protein of SEQ ID NO: 2 is a five-amino-acid-deleted-type HGF protein in which the five amino acid residues from amino acids 161 to 165 on the amino acid sequence shown in SEQ ID NO: 1 are deleted. The protein having the amino acid sequence of SEQ ID NO: 1 or 2 is a natural HGF protein of human origin which has the mitogen and motogen activities of HGF.

Proteins containing an amino acid sequence that is substantially the same as the amino acid sequence of SEQ ID NO: 1 or 2 are proteins containing an amino acid sequence with at least about 80%, preferably at least about 90%, and more preferably at least about 95% identity with the amino acid sequence of SEQ ID NO: 1 or 2. Preferred examples include proteins which act as HGF and have, relative to the amino acid sequence of SEQ ID NO: 1 or 2, an amino acid sequence wherein from one to a plurality of amino acid residues have been inserted or deleted, an amino acid sequence wherein from one to a plurality of amino acid residues have been substituted with other amino acid residues, or an amino acid sequence wherein from one to a plurality of amino acid residues have been modified. The inserted or substituted amino acids may be nonnatural amino acids other than the 20 types of amino acids encoded by genes. The nonnatural amino acids may be any compound having an amino group and a carboxyl group, such as γ-aminobutyric acid. These proteins may be used alone or as mixtures thereof. Examples of proteins containing an amino acid sequence that is substantially the same as the amino acid sequence of SEQ ID NO: 1 or 2 include, but are not limited to, the human HGF deposited in the NCBI database (NCBI-GenBank Flat File Release 164.0) under Accession Nos. BAA14348 and AAC71655.

HGF proteins that may be used in the present invention are preferably the above-described proteins of human origin for human application while use may also be made of HGF proteins from mammals other than man (e.g., monkey, cow, horse, pig, sheep, dog, cat, rat, mouse, rabbit, hamster, guinea pig, and chimpanzee). Illustrative examples of such HGF proteins include, but are not limited to, the following deposited in, for instance, the NCBI database: mouse HGF (e.g., Accession Nos. AAB31855, NP_034557, BAA01065, BAA01064), rat HGF (e.g., Accession No. NP_58713 (the protein having the amino acid sequence shown in SEQ ID NO: 3)), cow HGF (e.g., Accession Nos. NP_001026921, BAD02475), cat HGF (e.g., Accession Nos. NP_001009830, BAC10545, BAB21499), dog HGF (e.g., Accession Nos. NP_001002964, BAC57560), and chimpanzee HGF (e.g., Accession No. XP_519174).

The HGF protein used in the present invention may have a carboxyl group (—COOH), a carboxylate group (—COO⁻), an amide group (—CONH$_2$) or an ester group (—COOR) at the C-terminus. Here, the R in the ester is exemplified by $C_{1-6}$ alkyl groups such as methyl, ethyl, n-propyl, isopropyl and n-butyl; $C_{3-8}$ cycloalkyl groups such as cyclopentyl and cyclohexyl; $C_{6-12}$ aryl groups such as phenyl and α-naphthyl; $C_{7-14}$ aralkyl groups, including phenyl-$C_{1-2}$ alkyl groups such as benzyl and phenethyl, and α-naphthyl-$C_{1-2}$ alkyl groups such as α-naphthylmethyl; and pivaroyloxymethyl groups. The HGF protein of the present invention also includes an HGF protein having a carboxyl group (or carboxylate) at a site other than the C-terminus when the carboxyl group has been amidated or esterified. The ester in this case may be, for example, the above-mentioned C-terminal esters. HGF proteins which may be used in the invention include also any of the above-mentioned proteins wherein the amino group in the N-terminal methionine residue is protected with a protecting group (e.g., $C_{1-6}$ acyl groups, including formyl and $C_{2-6}$ alkanoyl groups such as acetyl), wherein the glutamyl group formed by in vivo cleavage of the N-terminus is converted to pyroglutamic acid, or wherein functional groups (e.g., —OH, —SH, amino group, imidazole group, indole group, guanidine group) on the side chains of amino acids in the molecule are protected with suitable protecting groups (e.g., $C_{1-6}$ acyl groups, including formyl and $C_{2-6}$ alkanoyl groups such as acetyl), and also complex proteins such as glycoproteins obtained by the bonding of sugar chains.

The HGF protein used in the invention may be in the form of a partial peptide thereof (sometimes referred to below simply as a "partial peptide"). Examples of such partial peptides include any protein that is a partial peptide of the above-mentioned HGF proteins and has substantially the same activity as HGF. In the present invention, preferred partial peptides include peptides containing an amino acid sequence of at least about 20, preferably at least about 50, and more preferably at least about 100 amino acids, from the amino acid sequence making up the above-mentioned HGF protein. Specific preferred examples include the peptide having the amino acid sequence from amino acid 32 to amino acid 210 starting on the N-terminal side of the human HGF amino acid sequence of SEQ ID NO: 1 (the sequence from the N-terminal hairpin loop on HGF to the first kringle domain), and the peptide having the amino acid sequence from amino acid 32 to amino acid 288 starting on the N-terminal side of the human HGF amino acid sequence of SEQ ID NO: 1 (the sequence from the N-terminal hairpin loop on HGF to the second kringle domain). In the partial peptide of the invention, the C-terminus may be a carboxyl group (—COOH), a carboxylate group (—COO⁻), an amide group (—CONH$_2$) or an ester group (—COOR). Moreover, the partial peptide, as with the above-mentioned HGF protein, encompasses partial peptides in which an amino group on the methionine residue at the N-terminus is protected with a protecting group, partial peptides in which Gln formed by in vivo cleavage of the N-terminus is converted to pyroglutamic acid, partial peptides in which functional groups on side chains of amino acids in the molecule are protected with suitable protecting groups, and also complex peptides such as glycopeptides obtained by the bonding of sugar chains.

Salts of the HGF proteins (including those in the form of partial peptides) that may be used in the invention are physiologically allowable salts with an acid or base. Physiologically allowable acid addition salts are especially preferred. Illustrative examples of such salts include salts with inorganic acids (e.g., hydrochloric acid, phosphoric acid, hydrobromic acid, sulfuric acid), and salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid).

When the HGF protein used in the invention is in the form of a partial peptide, this partial peptide may be prepared in accordance with a known peptide synthesis method or by cleaving an HGF protein with a suitable peptidase. Examples of suitable peptide synthesis methods include solid-phase synthesis and liquid-phase synthesis. In cases where partial peptides or amino acids capable of constituting the HGF protein are condensed with the remaining portions and the resulting product has protecting groups, the target peptide can be prepared by removing the protecting groups. Known condensation methods and methods of removing the protecting groups include those described by, for example, M. Bodanszky and M. A. Ondetti in Peptide Synthesis (Interscience Publishers: New York, 1966), and by Schroeder and Luebke in The Peptide (Academic Press: New York, 1965). Following the reaction, a partial peptide of the HGF protein can be purified and isolated by a conventional method of purification, such as a combination of solvent extraction, distillation, column chromatography, liquid chromatography and recrystallization. When the partial peptide obtained by the above method is a free acid or base, it can be converted into a suitable salt by a known method. Conversely, when it is obtained as a salt, it can be converted into a free acid or base by a known method.

The HGF protein used in the invention is preferably one of human origin for human application while the use of HGF protein derived from mammals other than man may also be used. An example of a suitable HGF protein of rat origin is shown in SEQ ID NO: 3.

The therapeutic agents of the invention, which are agents for treating spinal cord injuries and agents for treating demyelinating diseases, may be used in all neurological disorders accompanied by spin cord injury or demyelination. Specific examples include multiple sclerosis (MS), Device disease, Balo's concentric sclerosis, acute disseminated encephalomyelitis (ADEM), Schilder disease, subacute sclerosing panencephalitis (SSPE), progressive multifocal leukoencephalopathy (PML), Binswanger disease, hypoxic encephalopathy, central pontine myelinolysis, Guillain-Barre syndrome, Fischer syndrome, and chronic inflammatory demyelinating polyradiculoneuropathy (CIDP). Spinal cord injuries with associated demyelination are also encompassed herein.

The therapeutic agents of the invention (agents for treating spinal cord injuries and agents for treating demyelinating diseases) may be employed in not only humans, but also mammals other than humans (e.g., monkeys, cows, horses, pigs, sheep, dogs, and cats).

When the therapeutic agents of the invention (agents for treating spinal cord injuries and agents for treating demyelinating diseases) are to be administered to human or animal patients, they may be prepared in any of various dosage forms, such as liquid medications and solid medications. Generally, the HGF protein by itself or together with a conventional carrier is prepared in the form of, for example, an injectable drug, a spray, or a sustained-release preparation (e.g., depot preparations). The injectable drug may be an aqueous injectable drug or an oil-soluble injectable drug. If the injectable drug is an aqueous injectable drug, preparation may be carried out in accordance with a known method, such as by dissolving the HGF protein in a solution obtained by optionally adding, to an aqueous solvent (e.g., water for injection, purified water), pharmaceutically acceptable excipients, for example, tonicity agents (e.g., sodium chloride, potassium chloride, glycerin, mannitol, sorbitol, boric acid, borax, glucose, propylene glycol), buffers (e.g., phosphate buffer, acetate buffer, borate buffer, carbonate buffer, citrate buffer, Tris buffer, glutamate buffer, epsilon-aminocaproate buffer), preservatives (e.g., methyl paraoxybenzoate, ethyl paraoxybenzoate, propyl paraoxybenzoate, butyl paraoxybenzoate, chlorobutanol, benzyl alcohol, benzalkonium chloride, sodium dehydroacetate, edetate sodium, boric acid, borax), thickeners (e.g., hydroxyethyl cellulose, hydroxypropyl cellulose, polyvinyl alcohol, polyethylene glycol), stabilizers (e.g., sodium bisulfite, sodium thiosulfate, edetate sodium, sodium citrate, ascorbic acid, dibutylhydroxytoluene) and pH adjustors (e.g., hydrochloric acid, sodium hydroxide, phosphoric acid, acetic acid), followed by filtration with a filter or the like and sterilization, then filling into a sterile container. A suitable dissolution aid, such as an alcohol (e.g., ethanol), a polyalcohol (e.g., propylene glycol, polyethylene glycol), or a nonionic surfactant (e.g., polysorbate 80, polyoxyethylene-hardened castor oil 50) may also be used. If the injectable drug is an oil-soluble injectable drug, sesame oil or soybean oil may be used as the oleaginous solvent, and benzyl benzoate or benzyl alcohol may be use as the dissolution aid. The injectable drug that has been prepared is generally filled into an ampule or vial. The HGF protein content in the injectable drug is adjusted to generally from about 0.0002 to about 2.0 w/v %, preferably from about 0.001 to about 1.0 w/v %, and more preferably from about 0.01 to about 0.5 w/v %. Also, it is desirable for liquid preparations such as injectable drugs to be preserved by freezing or to be preserved after the removal of moisture by freeze drying or the like. At the time of use, distilled water for injection or the like is added to the freeze-dried preparation so as to redissolve the drug and prepare it for use.

Sprays may also be prepared in accordance with conventional practice for medicinal preparations. In the case of production as a spray, any additives commonly used in preparations to be inhaled may be employed. For example, aside from a propellant, use may be made of the above-mentioned solvents, preservatives, stabilizers, tonicity agents and pH adjustors. Propellants that may be used include liquefied gas propellants and compressed gas. Examples of liquefied gas propellants include fluorinated hydrocarbons (e.g., substitutes for CFC's, such as HCFC22, HCFC-123, HCFC-134a and HCFC142), liquefied petroleum and dimethyl ether. Illustrative examples of compressed gases include soluble gases (e.g., carbon dioxide, nitrous oxide) and insoluble gases (e.g., nitrogen gas).

The HGF protein used in the invention may be prepared as a sustained-release preparation (e.g., depot preparation) together with a biodegradable polymer. By preparing the HGF protein as a depot preparation in particular, a number of desirable effects can be expected, such as a decrease in the number of times it is administered, a good duration in the therapeutic effects, and the alleviation of side effects. Such sustained release preparations can be produced by a known method. The biodegradable polymer used in this sustained release preparation may be suitably selected from among known biodegradable polymers, such as polysaccharides, including starch, dextran, hyaluronan (hyaluronic acid) and salts thereof; proteins such as atelocollagen, collagen and gelatin; polyamino acids such as polyglutamic acid, polylysine, polyleucine, polyalanine and polymethionine; polylactic acid, polyglycolic acid, lactic acid-glycolic acid copolymers, polycaprolactone, poly-β-hydroxybutyricacid and polymalic acid; polyesters and polyorthoesters such as fumaric acid-polyethylene glycol-vinylpyrrolidone copolymers; polyalkylcyanoacrylic acids such as polymethyl-α-cyanoacrylic acid; and polycarbonates such as polyethylene carbonate and polypropylene carbonate. Polyesters are preferred, and lactic acid-glycolic acid copolymers are especially preferred. When lactic acid-glycolic acid copolymer is used, the compositional ratio (lactic acid/glycolic acid) thereof, in mol %, varies with the intended period of sustained release. For example, for a sustained release period of from about 2 weeks to about 3 months, and preferably from about 2 weeks to about 1 month, the ratio is in a range of from about 100/0 to about 50/50. The weight-average molecular weight of the lactic acid-glycolic acid copolymer is generally from about 5,000 to about 20,000. The lactic acid-glycolic acid copolymer may be produced by a known production method, such as that described in Japanese Patent Application Laid-open No. 61-28521. The compounding ratio of the biodegradable polymer and the HGF protein is not subject to any particular limitation. For example, the ratio of HGF protein to the biodegradable polymer is typically from about 0.01 to about 30 w/w %.

Administration is preferably carried out by, in the case of an injectable preparation or spray, direct injection (e.g., intrathecal administration, continuous intrathecal administration with a sustained-release pump) or spraying to the tissue affected by a spinal cord injury or demyelinating disease, or by, in the case of a sustained-release preparation (depot preparation), implantation of the preparation at a site near the tissue affected by a spinal cord injury or demyelinating disease. The dose is suitably selected according to such factors as the dosage form, severity of the disorder and the patient's age, and is generally from 1 µg to 500 mg, and preferably from 10 µg to 50 mg, per administration. The method of administration may also be suitably selected according to the dosage form, severity of the disorder, patient's age and other factors. For example, the therapeutic agent may be given as a single, one-time administration, as a single, sustained administration for a period ranging from about 30 minutes to several weeks (preferably for a period ranging from about 24 hours to about 2 weeks). Alternatively, the above one-time administration or sustained administration may be given repetitively at spaced intervals. In the case of repeated administration, the dosing interval may be from once a day to once every several months. For instance, in the case of administration as a sustained-release preparation (depot preparation) or in the case of local (e.g., intrathecal) sustained administration with a sustained-release pump (e.g., an osmotic pump), the dosing interval may be from several weeks to several months. Such sustained administration has the advantage that, since HGF protein is gradually released over an extended period of time at the site of spinal cord injury or demyelinating disease, the HGF acts over an extended period, enabling even better therapeutic effects to be achieved. A further advantage is that the less number of administrations eases the burden on the patient. A still further advantage is that, if necessary, additional HGF protein can be supplied to the subcutaneously implanted osmotic pump. As noted above, local administration is preferred as the method of administration, although other methods of administration such as intramuscular administration, subcutaneous administration or drip infusion are also possible. The period of administration is suitably selected according to such factors as the dosage forms, severity of the disorder and age of the patient. For example, in the case of a spinal cord injury, administration should take place preferably within 14 days, more preferably within 7 days, and most preferably within 4 days after the injury was sustained. In particular, in spinal cord injury patients, given how difficult it is to stabilize the condition of the patient within 72 hours following trauma, it is especially preferable for administration to take place from about 72 hours and within 4 days after the injury was sustained. The above period of administration includes the start of administration in the case of sustained administration, or the initial administration in the case of repetitive administration.

EXAMPLES

Examples are used below to describe the invention, although the invention is not limited by these examples. The HGF protein used in the following examples was a five-amino-acid-deleted-type recombinant HGF protein (SEQ ID NO: 2).

Example 1

Preparation of Spinal Cord Injury Animals and Administration of HGF Protein (1) Preparation of Spinal Cord Injury Animals
First, an osmotic pump was sterilely prepared for use. HGF protein (concentration: 1 mg/mL; dissolved in PBS) or PBS (control) was poured into an Alzet miniosmotic pump (Model 2002, manufactured by ALZA Corporation). Silicone tube (catheter tube, manufactured by Imamura Co., Ltd.) having an inner diameter of 0.3 mm and an outer diameter of 0.7 mm whose lumen was filled with HGF protein or PBS was connected to the pump outlet and the junction was covered with another silicone tube (Imamura Co., Ltd.) having an inner diameter of 1.0 mm and an outer diameter of 2.0 mm, following which the pump and tube assembly was incubated at 37° C. for 12 hours, then furnished for use in the experiment.

Adult, female Sprague-Dawley rats (ranging in age from about 10 to 12 weeks, and having a body weight of about 250 g) were anesthetized by the intraperitoneal administration of 14 w/v % chloral hydrate, and the tenth and twelfth thoracic vertebrae were laminectomized. An osmotic pump (prefilled with HGF protein solution by the method described above) was then implanted subcutaneously on the right dorsal side, and the catheter tube was passed through the muscle layer from the subcutaneous area. Thereafter, the tip of the catheter tube was advanced to the position of the arch of the twelfth thoracic vertebra. Next, a 200 kDyne crushing injury was created at the tenth thoracic spinal cord segment using an IH impactor (manufactured by Precision Systems). Thereafter, the dura mater and arachnoid membrane of the twelfth thoracic spinal cord were split together in the direction of craniocaudal axis, from which the catheter tube was inserted into the subarachnoid space and the tip of the catheter was advanced to the point of the damaged spinal cord. The catheter was immobilized at inner and outer sides of the muscle layer with the surgical adhesive Aron Alpha A Sankyo (available from Sankyo Co., Ltd.). After the adhesive fully dried, the muscle layer and the skin were respectively sutured, completing the operation.

(2) Administration of HGF Protein
Following the operation (following the crushing injury), HGF protein solution was intrathecally administered for 2 weeks by means of the above-described osmotic pump (HGF protein dose, 200 µg/2 weeks). A control group was given only PBS.

Example 2

Tissue Analysis and Results

After a fixed postoperative period, the rats were deeply anesthetized by the intraperitoneal administration of 14 w/v % chloral hydrate, following which perfusion from the left ventricle of the heart was carried out, first with PBS, and then with 4 w/v % paraformaldehyde/PBS. A piece of the spinal cord was removed and subsequently fixed in 4 w/v % paraformaldehyde/PBS for 24 hours at 4° C. The tissue sample was immersed in a 10 w/v % sucrose/PBS solution and then a 30 w/v % sucrose/PBS solution each at 4° C. and for 24 hours, after which it was embedded in OCT compound (Sakura Fine Technical). The embedded tissue was immediately frozen in liquid nitrogen, and 20 µm frozen sections were prepared. The tissue sections were then stained with hematoxylin and eosin (HE), and histological examination was carried out. As a result, as shown in FIG. 1, cavity formation due to motor neutron degeneration and cell death was clearly suppressed in the HGF protein group as compared with the control group, thus indicating that spinal cord degeneration from crushing was suppressed.

Example 3

Myelin Sheath Stain and Results

Figure 2:
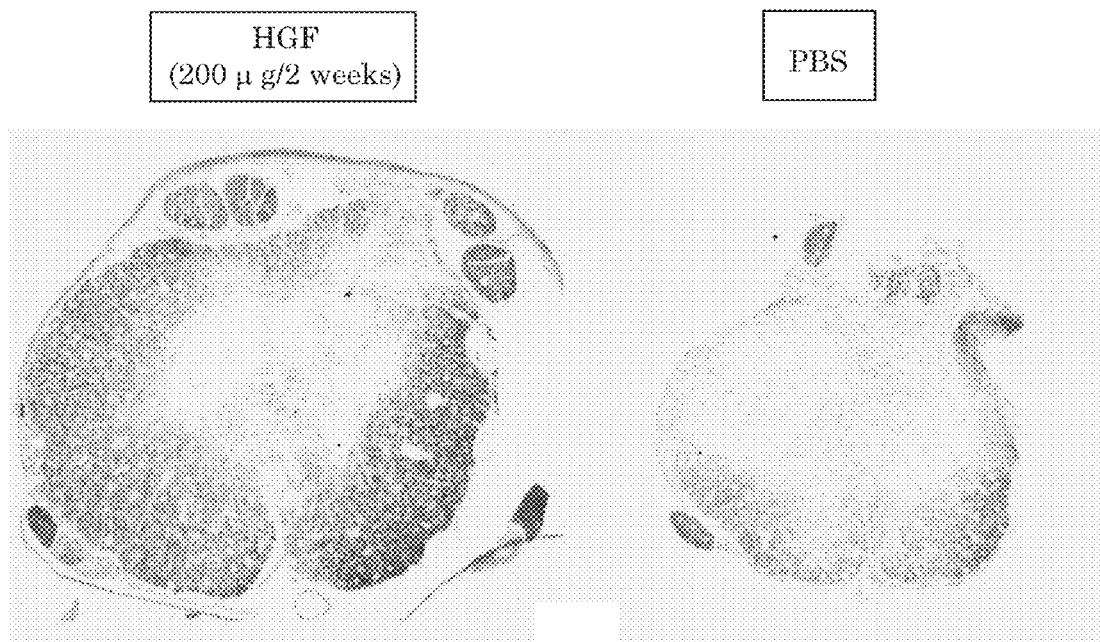
FIG. 2 shows Luxol Fast Blue (LFB) stained images of spinal cord tissue following a spinal cord injury from an HGF protein group given 200 µg/2 weeks of HGF protein starting immediately after spinal cord injury, and of spinal cord tissue from a control group.

The sections prepared by the method described in Example 2 were treated with 95 v/v % ethanol, following which they were incubated at 60° C. for 2 hours in a Luxor Fast Blue (LFB) solution. After removal from the incubator, the sections were left to stand to be cooled to room temperature and washed with 95 v/v % ethanol and distilled water. Next, fractionation with a lithium carbonate solution and 70 v/v % ethanol and washing with distilled water were repeatedly carried out until a suitable contrast was obtained, following which the sections were dehydrated and sealed, and the myelin sheath was examined. As shown in FIG. 2, the LFB-positive myelin sheath surface area in the HGF protein group was larger than that in the control group, indicating that demyelination due to spinal cord injury was suppressed.

Example 4

Immunohistochemical Analysis and Results

Figure 3:
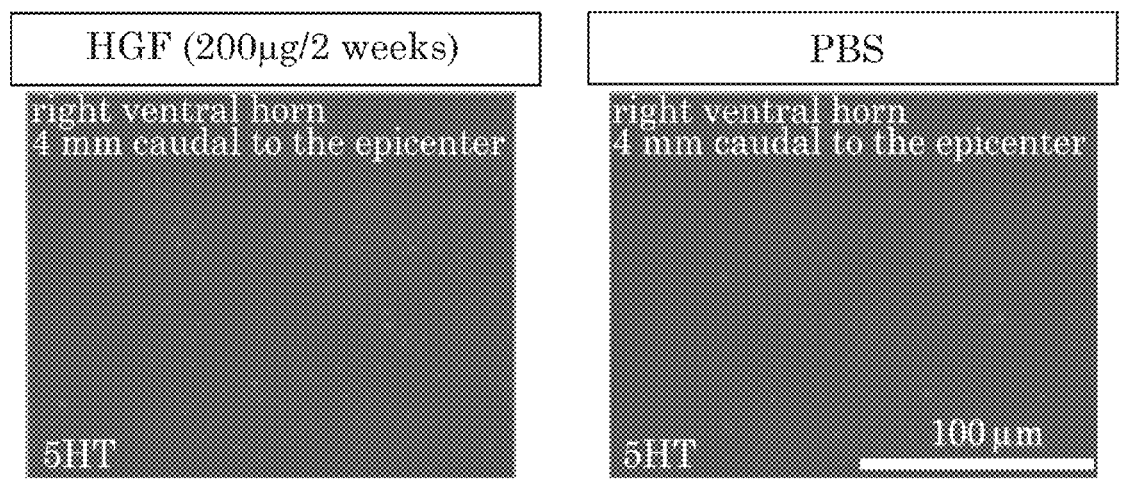
FIG. 3 shows 5-Hydroxytryptamine (5HT) stained images of spinal cord tissue following a spinal cord injury from an HGF protein group given 200 µg/2 weeks of HGF protein starting immediately after spinal cord injury, and of spinal cord tissue from a control group.
Figure 4:
FIG. 4 shows 5HT and Growth associated protein-43 (GAP43) stained images of spinal cord tissue following a spinal cord injury from an HGF protein group given 200 µg/2 weeks of HGF protein starting immediately after spinal cord injury.

The sections prepared by the method described in Example 2 were stained with polyclonal 5HT antibody (1:100 dilution) and polyclonal anti-GAP43 antibody (1:1000 dilution). That is, one hour of blocking at room temperature was carried out with PBS containing 5 v/v % goat serum and 0.1 w/v % Triton X-100, following which the sections were incubated overnight in the antibody solution at 4° C. These sections were washed with PBS, then incubated at room temperature for one hour in a secondary antibody that was fluorescently-labeled with Alexa 488 (green) and Alexa 546 (red (1:1000 dilution), and sealed on slides, and 5HT positive nerve fibers and GAP43 positive nerve fibers were examined under a fluorescence microscope. As a result, as shown in FIG. 3, 5HT-positive nerve fibers were found to be significantly more abundant 4 mm caudal to the site of injury in the HGF protein group as compared with the control group. Moreover, as shown in FIG. 4, there was good agreement between the localizations of 5HT positive signals and GAP43 positive signals. The fact that the 5HT positive nerve fibers are responsible for motor function following spinal cord injury and that, in adults, GAP43 is expressed only in regenerated nerve fibers indicated that the regeneration of nerve fibers linked to motor function was facilitated by the administration of HGF protein.

Example 5

Motor Function Evaluation and Results

Motor function of animals treated with HGF protein (200 µg/2 weeks) starting immediately after spinal cord injury, by the method described in Example 1, was examined using an open field test. Behavior of animals was visually observed by a plurality of observers, and evaluated using the Basso-Beattie-Bresnahan (BBB) score system, in which motor function is evaluated on a 21-step scale ranging from 0 (completely paralyzed) to 21 (normal). Hindlimb motor function was evaluated for 6 weeks postoperatively. The results are shown in FIG. 5.

Figure 5:
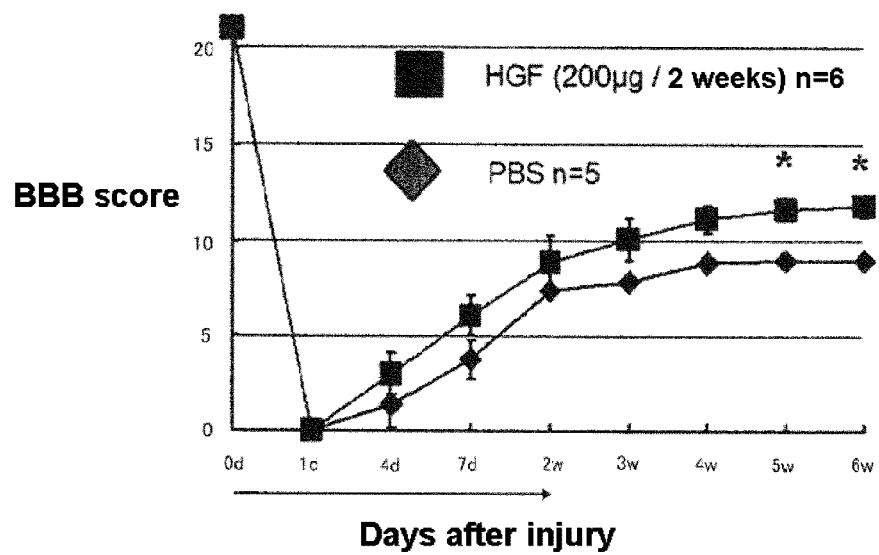
FIG. 5 is a line graph showing the Basso-Beattie-Bresnahan (BBB) scores following a spinal cord injury for an HGF protein group given 200 µg/2 weeks of HGF protein starting immediately after spinal cord injury and for a control group. In the graph, the arrow indicates the HGF protein or PBS dosing period.

From FIG. 5, it is apparent that functional recovery was observed starting at 4 days following spinal cord injury in the HGF protein group, and significant functional recovery effects compared to the control group were observed from 5 weeks on ($p<0.05$).

Example 6

Spinal cord injury animals were prepared in the same way as in Example 1, following which an osmotic pump filled with HGF protein (2 mg/mL, dissolved in PBS) or PBS (control) was implanted and catheter insertion were carried out. Postoperatively (following crushing injury), an HGF protein solution was intrathecally administered (HGF protein dose, 400 µg/4 weeks) for a period of 4 weeks with the osmotic pump. The control group was given PBS only. Motor functional evaluation by the method described in Example 5 was carried out up until 9 weeks following the operation. The results are shown in FIG. 6.

Figure 6:
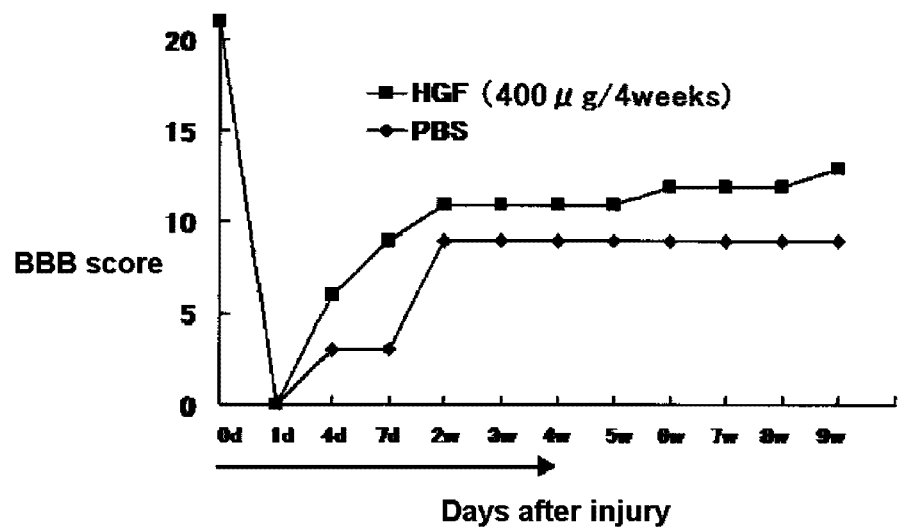
FIG. 6 is a line graph showing the BBB scores following a spinal cord injury for an HGF protein group given 400 µg/4 weeks of HGF protein starting immediately after spinal cord injury and for a control group. In the graph, the arrow indicates the HGF protein or PBS dosing period.

As is apparent from FIG. 6, functional recovery in animals treated with HGF protein was significantly promoted compared with the control animals. The difference was evident from 4 days after spinal cord injury. In addition, a rise in the BBB score continued even after the completion of administration of HGF protein.

Example 7

Adult, female Sprague-Dawley rats (ranging in age from about 10 to 12 weeks, and having a body weight of about 250 g) were anesthetized by the intraperitoneal administration of 14 w/v % chloral hydrate, and a 200 kDyne crushing injury was created at the tenth thoracic spinal cord segment using an IH impactor (manufactured by Precision Systems), thereby giving a spinal cord injured animal. The spinal cord injured animal was reoperated at 4 days, 2 weeks or 8 weeks following the crushing injury in order to implant an osmotic pump. An osmotic pump filled with HGF protein (2 mg/mL, dissolved in PBS) or PBS (control) was subcutaneously implanted by the same method as in Example 1 and the catheter tube was inserted into the subarachnoid space, following which the tip of the catheter tube was advanced to the point of the damaged spinal cord and finally the catheter was immobilized. Starting 4 days, 2 weeks or 8 weeks after the crushing injury, the HGF protein solution was intrathecally administered from the osmotic pump over a period of 4 weeks (HGF protein dose: 400 µg/4 weeks). In the control group, PBS alone was administered. Motor function evaluation over time was carried out by the same method as in Example 5. The results are shown in FIGS. 7, 8 and 9.

Figure 7:
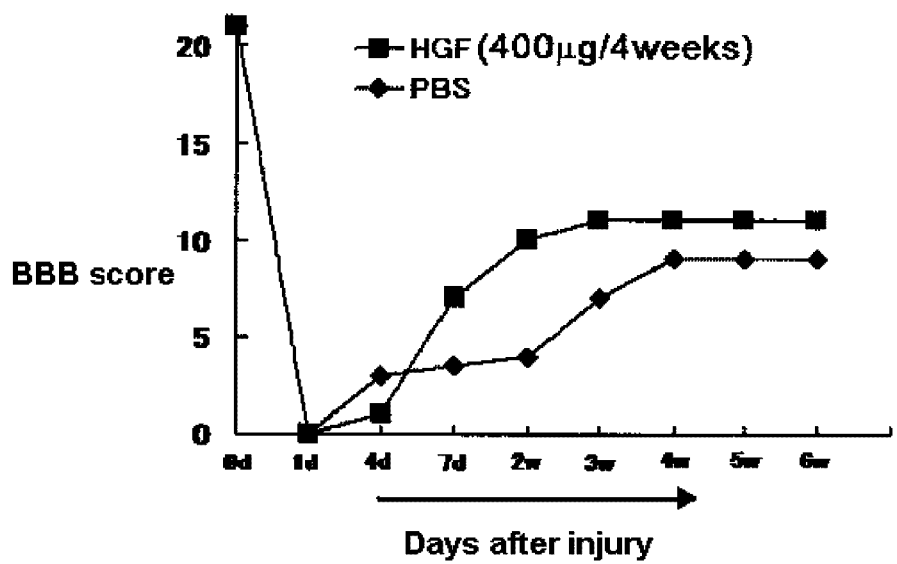
FIG. 7 is a line graph showing the BBB scores following a spinal cord injury for an HGF protein group given 400 µg/4 weeks of HGF protein starting 4 days after spinal cord injury and for a control group. In the graph, the arrow indicates the HGF protein or PBS dosing period.

In the animal group in which HGF treatment was started from 4 days after crushing injury, as is apparent from FIG. 7, faster functional recovery than in the control animals was observed.

Figure 8:
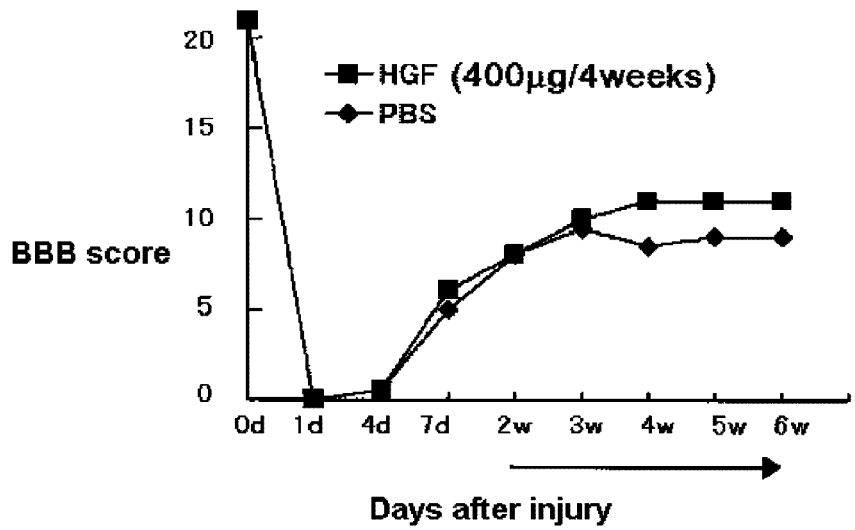
FIG. 8 is a line graph showing the BBB scores following a spinal cord injury for an HGF protein group given 400 µg/4 weeks of HGF protein starting 2 weeks after spinal cord injury and for a control group. In the graph, the arrow indicates the HGF protein or PBS dosing period.

In the animal group in which HGF treatment was started 2 weeks after the crushing injury, as is apparent from FIG. 8, the effect of promotion of functional recovery was observed 2 weeks after the start of HGF treatment (4 weeks after the crushing injury) in comparison with the control group.

Figure 9:
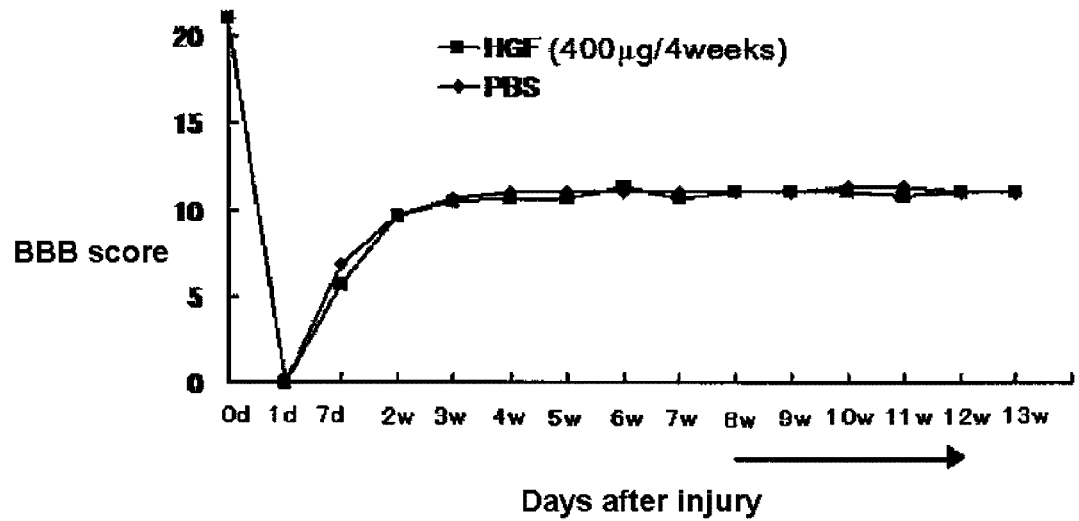
FIG. 9 is a line graph showing the BBB scores following a spinal cord injury for an HGF protein group given 400 µg/4 weeks of HGF protein starting 8 weeks after spinal cord injury and for a control group. In the graph, the arrow indicates the HGF protein or PBS dosing period.

In the animal group in which HGF treatment was started 8 weeks after the crushing injury, as is apparent from FIG. 9, no difference in functional recovery was observed between the animals given HGF protein and the control animals.

Preparation Example 1

A lactic acid-glycolic acid copolymer (1.9 g; lactic acid/glycolic acid=50/50; weight-average molecular weight=10,000; available from Wako Pure Chemical Industries, Ltd.) was dissolved in 3.0 mL of dichloromethane. Next, 100 mg of a freeze-dried powder of HGF protein was added to this organic solvent solution and finely milled using a mixer mill (Retsch Technology), thereby preparing an HGF protein dispersion. The dispersion was added to 800 mL of a 0.1 w/v % aqueous polyvinyl alcohol solution, then agitated and homogenized using a homomixer. The dichloromethane was evaporated off by 3 hours of stirring at room temperature, following which the microcapsules were collected by centrifugation at about 2,000 rpm. The microcapsules were then washed twice using 400 mL of distilled water, following which 0.2 g of D-mannitol was added and freeze-drying was carried out. To remove residual solvent, vacuum-drying was carried out for 3 days at 40° C., thereby giving HGF protein-containing sustained-release microcapsules (HGF proportion based on biopolymer: 5.3 w/w %).

Preparation Example 2

A lactic acid-glycolic acid copolymer (1.89 g; lactic acid/glycolic acid=50/50; weight-average molecular weight=10,000; available from Wako Pure Chemical Industries, Ltd.) and 10 mg of zinc oxide were dissolved in 3.0 mL of dichloromethane. Next, 100 mg of a freeze-dried powder of HGF protein was added to this organic solvent solution and finely milled using a mixer mill (Retsch Technology), thereby preparing an HGF protein dispersion. The dispersion was added to 800 mL of a 0.1 w/v % aqueous polyvinyl alcohol solution, then agitated and homogenized using a homomixer. The dichloromethane was evaporated off by 3 hours of stirring at room temperature, following which the microcapsules were collected by centrifugation at about 2,000 rpm. The microcapsules were then washed twice using 400 mL of distilled water, following which 0.2 g of D-mannitol was added and freeze-drying was carried out. To remove residual solvent, vacuum-drying was carried out for 3 days at 40° C., thereby giving HGF protein-containing sustained-release microcapsules (HGF proportion based on biopolymer: 5.3 w/w %).

Preparation Example 3

A lactic acid-glycolic acid copolymer (1.7 g; lactic acid/glycolic acid=75/25; weight-average molecular weight=15,000; available from Wako Pure Chemical Industries, Ltd.) was dissolved in 2.7 mL of dichloromethane. Next, 300 mg of a freeze-dried powder of HGF protein was added to this organic solvent solution and finely milled using a mixer mill (Retsch Technology), thereby preparing an HGF protein dispersion. The dispersion was added to 800 mL of a 0.1 w/v % aqueous polyvinyl alcohol solution, then agitated and homogenized using a homomixer. The dichloromethane was evaporated off by 3 hours of stirring at room temperature, following which the microcapsules were collected by centrifugation at about 2,000 rpm. The microcapsules were then washed twice using 400 mL of distilled water, following which 0.2 g of D-mannitol was added and freeze-drying was carried out. To remove residual solvent, vacuum-drying was carried out for 3 days at 40° C., thereby giving HGF protein-containing sustained-release microcapsules (HGF proportion based on biopolymer: 17.6 w/w %).

Preparation Example 4

A lactic acid-glycolic acid copolymer (1.69 g; lactic acid/glycolic acid=75/25; weight-average molecular weight=15,000; available from Wako Pure Chemical Industries, Ltd.) and 10 mg of zinc oxide were dissolved in 2.7 mL of dichloromethane. Next, 300 mg of a freeze-dried powder of HGF protein was added to this organic solvent solution and finely milled using a mixer mill (Retsch Technology), thereby preparing an HGF protein dispersion. The dispersion was added to 800 mL of a 0.1 w/v % aqueous polyvinyl alcohol solution, then agitated and homogenized using a homomixer. The dichloromethane was evaporated off by 3 hours of stirring at room temperature, following which the microcapsules were collected by centrifugation at about 2,000 rpm. The microcapsules were then washed twice using 400 mL of distilled water, following which 0.2 g of D-mannitol was added and freeze-drying was carried out. To remove residual solvent, vacuum-drying was carried out for 3 days at 40° C., thereby giving HGF protein-containing sustained-release microcapsules (HGF proportion based on biopolymer: 17.8 w/w %).

Preparation Example 5

A DL-lactic acid polymer (5 g; lactic acid/glycolic acid=100/0; weight-average molecular weight=5,000; available from Wako Pure Chemical Industries, Ltd.) was dissolved in 50 mL of methylene chloride, thereby preparing a 10 w/v % solution. Next, 2.5 mg of a freeze-dried powder of HGF protein was added to the solution. The resulting mixture was then added to a 0.5 w/v % aqueous solution of chitosan that had been separately warmed to 40° C., following which agitation and emulsification were carried out at a stirring speed of 1000 rpm using a homomixer. The resulting emulsion was stirred for another 3 hours at room temperature to evaporate off the methylene chloride, following which the microspheres that formed were collected by centrifugation at about 2,000 rpm. The microspheres were washed five times using distilled water that had been pre-warmed to 40° C., then vacuum-dried at room temperature, thereby giving HGF protein-containing microspheres (HGF proportion based on biopolymer: 0.05 w/w %).

Preparation Example 6

A lactic acid-glycolic acid copolymer (10 g; lactic acid/glycolic acid=75/25; weight-average molecular weight=5,000; available from Wako Pure Chemical Industries, Ltd.) was dissolved in 200 mL of methylene chloride/ethanol (4:1), thereby preparing a 5 w/v % solution. To this solution was added 2.5 mg of a freeze-dried powder of HGF protein. The resulting mixture was added a little at a time, under agitation with a homomixer at a speed of 500 rpm, to a 1 w/v % aqueous gelatin solution that was separately warmed to 40° C., thereby effecting emulsification. The resulting emulsion was additionally stirred at room temperature for 3 hours to evaporate off the methylene chloride and ethanol, following which the microspheres that formed were collected by centrifugation at about 2,000 rpm, washed five times with distilled water that had been pre-warmed to 40° C., and vacuum-dried at room temperature, thereby giving HGF protein-containing microspheres (HGF proportion based on biopolymer: 0.025 w/w %).

Preparation Example 7

A 2 w/v % aqueous solution of HGF protein (0.2 mL) was mixed with 2 mL of a 2% phosphate buffer solution of atelocollagen, and freeze-dried. The freeze-dried material was fractured at low temperature using liquid nitrogen, then placed in a mold and compression-molded to form a cylindrical HGF-containing sustained-released preparation (HGF proportion based on biopolymer: 10 w/w %).

Preparation Example 8

A 0.01 w/v % aqueous solution of HGF protein (100 mL) and 50 g of a 2 w/v % aqueous solution of collagen were uniformly mixed together and agitated, and then freeze-dried. The freeze-dried material was low-temperature fractured using liquid nitrogen, following which the fractured material was compression molded into a stick, thereby giving an HGF-containing sustained-released preparation (HGF proportion based on biopolymer: 1 w/w %).

Preparation Example 9

HGF protein (1 mg) was dissolved in 2 ml of a 2 w/v % atelocollagen solution, following which freeze drying was carried out. The resulting composite was fractured, and then compression-molded into a cylindrical shape, giving an HGF-containing sustained-release preparation (HGF proportion based on biopolymer, 2.5 wt %).

Preparation Example 10

The sodium salt of hyaluronan (0.58 g; intrinsic viscosity, 4500 cc/g) was mixed with 20 mL of water and made to swell.

Next, 2 mL of 2N sodium hydroxide was added to this mixture, and stirring was carried out to give a uniform solution. Divinylsulfone (0.10 g) in 2.4 mL of water was then added and stirred. The resulting mixture was left to stand for 70 minutes, after which the gel that formed was placed in 223 mL of a Biotris buffer solution (a phosphate buffer containing 0.15 M of NaCl and having a pH of about 7.2), and swelling was induced for 3 hours. Next, 1 mL of 2N HCl was added to this mixture. After 1 hour, 0.6 mL of 2 N HCl was added, and the mixture was left to stand for 16 hours. This was followed by the addition of 0.35 mL of 2N HCl, after which the swelled gel was slowly stirred in the buffer solution for 3 days. A soft gel having uniform viscoelastic properties was obtained. The gel was dialyzed with 0.15 M NaCl for 5 days. The gel was then mixed with 1 w/v % HGF protein in buffered saline so as to set the final concentration of HGF protein to 0.25 w/v %, thereby giving an HGF-containing preparation (HGF proportion based on biopolymer: 25 w/v %).

INDUSTRIAL APPLICABILITY

The present invention provides an agent useful for treating spinal cord injuries and demyelinating diseases.

What is claimed is:

1. A method of improving motor function in a human or an animal having a spinal cord injury comprising:
   selecting a subject who/which is a human or an animal having a spinal cord injury; and
   providing said human or animal with a hepatocyte growth factor (HGF) preparation of which active ingredient is an HGF protein by intrathecal administration to improve motor function in the human or animal having a spinal cord injury,
   the HGF being selected from the group consisting of (a) HGF having the amino acid sequence of SEQ ID NO:1, (b) HGF having the amino acid sequence of SEQ ID NO:2, (c) HGF having an amino acid sequence with at least 95% identity with the amino acid sequence of SEQ ID NO:1 and possessing HGF activity, (d) HGF having an amino acid sequence with at least 95% identity with the amino acid sequence of SEQ ID NO:2 and possessing HGF activity, (e) HGF produced by a method that comprises integrating a gene encoding the amino acid sequence of SEQ ID NO:1 into a vector; transforming a host cell with the vector; expressing a recombinant HGF from the vector; and obtaining a recombinant HGF from a culture supernatant of the transformant, and (f) HGF produced by a method that comprises integrating a gene encoding the amino acid sequence of SEQ ID NO:2 into a vector; transforming a host cell with the vector; expressing a recombinant HGF from the vector; and obtaining a recombinant HGF from a culture supernatant of the transformant.

2. The method of claim 1, wherein said HGF preparation is provided at a dose from 1 μg to 500 mg per administration.

3. The method of claim 1, wherein said spinal cord injury is a traumatic spinal cord injury.

4. A method of improving motor function in a human or an animal having a spinal cord injury comprising:
   selecting a subject who/which is a human or an animal having a spinal cord injury; and
   providing said human or animal with a hepatocyte growth factor (HGF) preparation of which active ingredient is an HGF protein by implantation at a site near the tissue affected by the spinal cord injury to improve motor function in the human or animal having a spinal cord injury,
   the HGF being selected from the group consisting of (a) HGF having the amino acid sequence of SEQ ID NO:1, (b) HGF having the amino acid sequence of SEQ ID NO:2, (c) HGF having an amino acid sequence with at least 95% identity with the amino acid sequence of SEQ ID NO:1 and possessing HGF activity, (d) HGF having an amino acid sequence with at least 95% identity with the amino acid sequence of SEQ ID NO:2 and possessing HGF activity, (e) HGF produced by a method that comprises integrating a gene encoding the amino acid sequence of SEQ ID NO:1 into a vector; transforming a host cell with the vector; expressing a recombinant HGF from the vector; and obtaining a recombinant HGF from a culture supernatant of the transformant, and (f) HGF produced by a method that comprises integrating a gene encoding the amino acid sequence of SEQ ID NO:2 into a vector; transforming a host cell with the vector; expressing a recombinant HGF from the vector; and obtaining a recombinant HGF from a culture supernatant of the transformant,
   said hepatocyte growth factor (HGF) preparation comprising the HGF protein and a biopolymer, wherein said biopolymer is a lactic acid-glycolic acid copolymer having a weight average molecular weight from about 5,000 to about 20,000 Daltons and wherein the proportion of HGF to the biopolymer in said HGF preparation is from about 0.01 to about 30 w/w %.

5. A method of improving motor function in a human or an animal having a spinal cord injury comprising:
   selecting a subject who/which is a human or an animal having a spinal cord injury; and
   providing said human or animal with a hepatocyte growth factor (HGF) preparation of which active ingredient is an HGF protein by implantation at a site near the tissue affected by the spinal cord injury to improve motor function in the human or animal having a spinal cord injury,
   the HGF being selected from the group consisting of (a) HGF having the amino acid sequence of SEQ ID NO:1, (b) HGF having the amino acid sequence of SEQ ID NO:2, (c) HGF having an amino acid sequence with at least 95% identity with the amino acid sequence of SEQ ID NO:1 and possessing HGF activity, (d) HGF having an amino acid sequence with at least 95% identity with the amino acid sequence of SEQ ID NO:2 and possessing HGF activity, (e) HGF produced by a method that comprises integrating a gene encoding the amino acid sequence of SEQ ID NO:1 into a vector; transforming a host cell with the vector; expressing a recombinant HGF from the vector; and obtaining a recombinant HGF from a culture supernatant of the transformant, and (f) HGF produced by a method that comprises integrating a gene encoding the amino acid sequence of SEQ ID NO:2 into a vector; transforming a host cell with the vector; expressing a recombinant HGF from the vector; and obtaining a recombinant HGF from a culture supernatant of the transformant,
   said hepatocyte growth factor (HGF) preparation comprising the HGF protein and a biopolymer, wherein said biopolymer is a biodegradable polymer selected from the group consisting of a lactic acid polymer, lactic acid-glycolic acid copolymer, atelocollagen, collagen, and hyaluronan.

* * * * *

UNITED STATES PATENT AND TRADEMARK OFFICE
CERTIFICATE OF CORRECTION

PATENT NO.         : 8,518,880 B2
APPLICATION NO.    : 12/548881
DATED              : August 27, 2013
INVENTOR(S)        : Hideyuki Okano et al.

It is certified that error appears in the above-identified patent and that said Letters Patent is hereby corrected as shown below:

In the Specification

At Column 1, Line 24, please change "ingredient" to --ingredient.--.

At Column 2, Line 9, please change "Creutzfeldt-Jacov" to --Creutzfeldt-Jakob--.

At Column 7, Line 37, please change "pivaroyloxymethyl" to --pivaloyloxymethyl--.

At Column 9, Line 49, please change "use" to --used--.

Signed and Sealed this
Seventh Day of October, 2014

Michelle K. Lee
*Deputy Director of the United States Patent and Trademark Office*

```
                             SEQUENCE LISTING

<160> NUMBER OF SEQ ID NOS: 3

<210> SEQ ID NO 1
<211> LENGTH: 728
<212> TYPE: PRT
<213> ORGANISM: Homo sapiens

<400> SEQUENCE: 1

Met Trp Val Thr Lys Leu Leu Pro Ala Leu Leu Leu Gln His Val Leu
1               5                   10                  15

Leu His Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270
```

-continued

```
Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700
```

```
Ile Phe Val Arg Val Ala Tyr Tyr Ala Lys Trp Ile His Lys Ile Ile
705                 710                 715                 720

Leu Thr Tyr Lys Val Pro Gln Ser
                725
```

<210> SEQ ID NO 2
<211> LENGTH: 723
<212> TYPE: PRT
<213> ORGANISM: Homo sapiens

<400> SEQUENCE: 2

```
Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
            180                 185                 190

Tyr Glu Val Cys Asp Ile Pro Gln Cys Ser Glu Val Glu Cys Met Thr
        195                 200                 205

Cys Asn Gly Glu Ser Tyr Arg Gly Leu Met Asp His Thr Glu Ser Gly
210                 215                 220

Lys Ile Cys Gln Arg Trp Asp His Gln Thr Pro His Arg His Lys Phe
225                 230                 235                 240

Leu Pro Glu Arg Tyr Pro Asp Lys Gly Phe Asp Asp Asn Tyr Cys Arg
                245                 250                 255

Asn Pro Asp Gly Gln Pro Arg Pro Trp Cys Tyr Thr Leu Asp Pro His
            260                 265                 270

Thr Arg Trp Glu Tyr Cys Ala Ile Lys Thr Cys Ala Asp Asn Thr Met
        275                 280                 285

Asn Asp Thr Asp Val Pro Leu Glu Thr Thr Glu Cys Ile Gln Gly Gln
290                 295                 300

Gly Glu Gly Tyr Arg Gly Thr Val Asn Thr Ile Trp Asn Gly Ile Pro
305                 310                 315                 320

Cys Gln Arg Trp Asp Ser Gln Tyr Pro His Glu His Asp Met Thr Pro
                325                 330                 335

Glu Asn Phe Lys Cys Lys Asp Leu Arg Glu Asn Tyr Cys Arg Asn Pro
            340                 345                 350
```

```
Asp Gly Ser Glu Ser Pro Trp Cys Phe Thr Thr Asp Pro Asn Ile Arg
        355                 360                 365

Val Gly Tyr Cys Ser Gln Ile Pro Asn Cys Asp Met Ser His Gly Gln
    370                 375                 380

Asp Cys Tyr Arg Gly Asn Gly Lys Asn Tyr Met Gly Asn Leu Ser Gln
385                 390                 395                 400

Thr Arg Ser Gly Leu Thr Cys Ser Met Trp Asp Lys Asn Met Glu Asp
                405                 410                 415

Leu His Arg His Ile Phe Trp Glu Pro Asp Ala Ser Lys Leu Asn Glu
            420                 425                 430

Asn Tyr Cys Arg Asn Pro Asp Asp Ala His Gly Pro Trp Cys Tyr
        435                 440                 445

Thr Gly Asn Pro Leu Ile Pro Trp Asp Tyr Cys Pro Ile Ser Arg Cys
    450                 455                 460

Glu Gly Asp Thr Thr Pro Thr Ile Val Asn Leu Asp His Pro Val Ile
465                 470                 475                 480

Ser Cys Ala Lys Thr Lys Gln Leu Arg Val Val Asn Gly Ile Pro Thr
                485                 490                 495

Arg Thr Asn Ile Gly Trp Met Val Ser Leu Arg Tyr Arg Asn Lys His
            500                 505                 510

Ile Cys Gly Gly Ser Leu Ile Lys Glu Ser Trp Val Leu Thr Ala Arg
        515                 520                 525

Gln Cys Phe Pro Ser Arg Asp Leu Lys Asp Tyr Glu Ala Trp Leu Gly
    530                 535                 540

Ile His Asp Val His Gly Arg Gly Asp Glu Lys Cys Lys Gln Val Leu
545                 550                 555                 560

Asn Val Ser Gln Leu Val Tyr Gly Pro Glu Gly Ser Asp Leu Val Leu
                565                 570                 575

Met Lys Leu Ala Arg Pro Ala Val Leu Asp Asp Phe Val Ser Thr Ile
            580                 585                 590

Asp Leu Pro Asn Tyr Gly Cys Thr Ile Pro Glu Lys Thr Ser Cys Ser
        595                 600                 605

Val Tyr Gly Trp Gly Tyr Thr Gly Leu Ile Asn Tyr Asp Gly Leu Leu
    610                 615                 620

Arg Val Ala His Leu Tyr Ile Met Gly Asn Glu Lys Cys Ser Gln His
625                 630                 635                 640

His Arg Gly Lys Val Thr Leu Asn Glu Ser Glu Ile Cys Ala Gly Ala
                645                 650                 655

Glu Lys Ile Gly Ser Gly Pro Cys Glu Gly Asp Tyr Gly Gly Pro Leu
            660                 665                 670

Val Cys Glu Gln His Lys Met Arg Met Val Leu Gly Val Ile Val Pro
        675                 680                 685

Gly Arg Gly Cys Ala Ile Pro Asn Arg Pro Gly Ile Phe Val Arg Val
    690                 695                 700

Ala Tyr Tyr Ala Lys Trp Ile His Lys Ile Ile Leu Thr Tyr Lys Val
705                 710                 715                 720

Pro Gln Ser
```

<210> SEQ ID NO 3
<211> LENGTH: 728
<212> TYPE: PRT
<213> ORGANISM: Rattus norvegicus

<400> SEQUENCE: 3

```
Met Met Trp Gly Thr Lys Leu Leu Pro Val Leu Leu Leu Gln His Val
1               5                   10                  15

Leu Leu His Leu Leu Leu Pro Val Thr Ile Pro Tyr Ala Glu Gly
            20                  25                  30

Gln Lys Lys Arg Arg Asn Thr Leu His Glu Phe Lys Lys Ser Ala Lys
            35                  40                  45

Thr Thr Leu Thr Lys Glu Asp Pro Leu Val Lys Ile Lys Thr Lys Lys
    50                  55                  60

Val Asn Ser Ala Asp Glu Cys Ala Asn Arg Cys Ile Arg Asn Lys Gly
65              70                  75                  80

Phe Pro Phe Thr Cys Lys Ala Phe Val Phe Asp Lys Ser Arg Lys Arg
                85                  90                  95

Cys Tyr Trp Tyr Pro Phe Asn Ser Met Ser Ser Gly Val Lys Lys Gly
            100                 105                 110

Phe Gly His Glu Phe Asp Leu Tyr Glu Asn Lys Asp Tyr Ile Arg Asn
            115                 120                 125

Cys Ile Ile Gly Lys Gly Gly Ser Tyr Lys Gly Thr Val Ser Ile Thr
130                 135                 140

Lys Ser Gly Ile Lys Cys Gln Pro Trp Asn Ser Met Ile Pro His Glu
145                 150                 155                 160

His Ser Phe Leu Pro Ser Ser Tyr Arg Gly Lys Asp Leu Gln Glu Asn
                165                 170                 175

Tyr Cys Arg Asn Pro Arg Gly Glu Glu Gly Gly Pro Trp Cys Phe Thr
            180                 185                 190

Ser Asn Pro Glu Val Arg Tyr Glu Val Cys Asp Ile Pro Gln Cys Ser
            195                 200                 205

Glu Val Glu Cys Met Thr Cys Asn Gly Glu Ser Tyr Arg Gly Pro Met
210                 215                 220

Asp His Thr Glu Ser Gly Lys Thr Cys Gln Arg Trp Asp Gln Gln Thr
225                 230                 235                 240

Pro His Arg His Lys Phe Leu Pro Glu Arg Tyr Pro Asp Lys Gly Phe
                245                 250                 255

Asp Asp Asn Tyr Cys Arg Asn Pro Asp Gly Lys Pro Arg Pro Trp Cys
            260                 265                 270

Tyr Thr Leu Asp Pro Asp Thr Pro Trp Glu Tyr Cys Ala Ile Lys Met
            275                 280                 285

Cys Ala His Ser Ala Val Asn Glu Thr Asp Val Pro Met Glu Thr Thr
290                 295                 300

Glu Cys Ile Lys Gly Gln Gly Glu Gly Tyr Arg Gly Thr Thr Asn Thr
305                 310                 315                 320

Ile Trp Asn Gly Ile Pro Cys Gln Arg Trp Asp Ser Gln Tyr Pro His
                325                 330                 335

Lys His Asp Ile Thr Pro Glu Asn Phe Lys Cys Lys Asp Leu Arg Glu
            340                 345                 350

Asn Tyr Cys Arg Asn Pro Asp Gly Ala Glu Ser Pro Trp Cys Phe Thr
            355                 360                 365

Thr Asp Pro Asn Ile Arg Val Gly Tyr Cys Ser Gln Ile Pro Lys Cys
            370                 375                 380

Asp Val Ser Ser Gly Gln Asp Cys Tyr Arg Gly Asn Gly Lys Asn Tyr
385                 390                 395                 400

Met Gly Asn Leu Ser Lys Thr Arg Ser Gly Leu Thr Cys Ser Met Trp
                405                 410                 415
```

-continued

```
Asp Lys Asn Met Glu Asp Leu His Arg His Ile Phe Trp Glu Pro Asp
            420                 425                 430

Ala Ser Lys Leu Thr Lys Asn Tyr Cys Arg Asn Pro Asp Asp Ala
        435                 440                 445

His Gly Pro Trp Cys Tyr Thr Gly Asn Pro Leu Val Pro Trp Asp Tyr
    450                 455                 460

Cys Pro Ile Ser Arg Cys Glu Gly Asp Thr Thr Pro Thr Ile Val Asn
465                 470                 475                 480

Leu Asp His Pro Val Ile Ser Cys Ala Lys Thr Lys Gln Leu Arg Val
                485                 490                 495

Val Asn Gly Ile Pro Thr Gln Thr Thr Val Gly Trp Met Val Ser Leu
            500                 505                 510

Lys Tyr Arg Asn Lys His Ile Cys Gly Gly Ser Leu Ile Lys Glu Ser
        515                 520                 525

Trp Val Leu Thr Ala Arg Gln Cys Phe Pro Ala Arg Asn Lys Asp Leu
    530                 535                 540

Lys Asp Tyr Glu Ala Trp Leu Gly Ile His Asp Val His Glu Arg Gly
545                 550                 555                 560

Glu Glu Lys Arg Lys Gln Ile Leu Asn Ile Ser Gln Leu Val Tyr Gly
                565                 570                 575

Pro Glu Gly Ser Asp Leu Val Leu Leu Lys Leu Ala Arg Pro Ala Ile
            580                 585                 590

Leu Asp Asn Phe Val Ser Thr Ile Asp Leu Pro Ser Tyr Gly Cys Thr
        595                 600                 605

Ile Pro Glu Lys Thr Thr Cys Ser Ile Tyr Gly Trp Gly Tyr Thr Gly
    610                 615                 620

Leu Ile Asn Ala Asp Gly Leu Leu Arg Val Ala His Leu Tyr Ile Met
625                 630                 635                 640

Gly Asn Glu Lys Cys Ser Gln His His Gln Gly Lys Val Thr Leu Asn
                645                 650                 655

Glu Ser Glu Leu Cys Ala Gly Ala Glu Lys Ile Gly Ser Gly Pro Cys
            660                 665                 670

Glu Gly Asp Tyr Gly Gly Pro Leu Ile Cys Glu Gln His Lys Met Arg
        675                 680                 685

Met Val Leu Gly Val Ile Val Pro Gly Arg Gly Cys Ala Ile Pro Asn
    690                 695                 700

Arg Pro Gly Ile Phe Val Arg Val Ala Tyr Tyr Ala Lys Trp Ile His
705                 710                 715                 720

Lys Val Ile Leu Thr Tyr Lys Leu
                725
```